US00PP16164P2

(12) United States Plant Patent
Hansson

(10) Patent No.: US PP16,164 P2
(45) Date of Patent: Dec. 13, 2005

(54) *OSTEOSPERMUM* PLANT NAMED 'SEKIIN47'

(50) Latin Name: *Osteospermum ecklonis*
Varietal Denomination: Sekiin47

(76) Inventor: Jorn Hansson, Holmevej 36, 5471 Sondersoe (DK)

( * ) Notice: Subject to any disclaimer, the term of this patent is extended or adjusted under 35 U.S.C. 154(b) by 1 day.

(21) Appl. No.: 10/949,948

(22) Filed: Sep. 24, 2004

(51) Int. Cl.[7] ..... A01H 5/00

(52) U.S. Cl. ..... Plt./360

(58) Field of Search ..... Plt./360

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Osteospermum* plant named 'Sekiin47', characterized by its compact, mounded and outwardly spreading plant habit; freely branching habit; freely flowering habit; and intense yellow-colored ray florets with dark violet blue towards the base and dark purple-tipped disc florets.

1 Drawing Sheet

CROSS-REFERENCE TO RELATED APPLICATIONS

The present application is co-pending with the following related application entitled *Osteospermum* Plant Named 'Seipepan'; Jorn Hansson, applicant.

Botanical classification/cultivar designation: *Osteospermum ecklonis* cultivar Sekiin47.

BACKGROUND OF THE INVENTION

The present Invention relates to a new and distinct cultivar of *Osteospermum* plant, botanically known as *Osteospermum ecklonis*, and hereinafter referred to by the name 'Sekiin47'.

The new *Osteospermum* was discovered as a naturally-occurring whole plant mutation of the *Osteospermum ecklonis* cultivar Seikilrem, disclosed in U.S. Plant Pat. No. 13,407.

The new *Osteospermum* was discovered and selected by the Inventor in May, 2001, as a single flowering plant within a population of plants of the parent cultivar in a controlled environment in Germany.

Asexual reproduction of the new *Osteospermum* by terminal vegetative cuttings was first conducted in Sondersoe, Denmark in August, 2001. Asexual reproduction by cuttings has shown that the unique features of this new *Osteospermum* are stable and reproduced true to type in successive generations.

SUMMARY OF THE INVENTION

The cultivar Sekiin47 has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Sekiin47'. These characteristics in combination distinguish 'Sekiin47' as a new and distinct *Osteospermum:*

1. Compact, mounded and outwardly spreading plant habit.
2. Freely branching habit.

3. Freely flowering habit.
4. Intense yellow-colored ray florets with dark violet blue towards the base and dark purple-tipped disc florets.

Plants of the new *Osteospermum* differ primarily from plants of the parent, the cultivar Seikilrem, in ray floret coloration.

Plants of the new *Osteospermum* differ primarily from plants of the cultivar Seipepan, disclosed in a U.S. Plant patent application Ser. No. 10/949,950 filed concurrently, in ray floret coloration.

Plants of the new *Osteospermum* are similar in ray floret coloration to plants of the cultivar Cape Daisy Zulu, disclosed in U.S. Plant Pat. No. 10,389. However, plants of the new *Osteospermum* are more outwardly spreading and more freely flowering than plants of the cultivar Cape Daisy Zulu.

BRIEF DESCRIPTION OF THE PHOTOGRAPHS

The accompanying colored photographs illustrate the overall appearance of the new *Osteospermum* showing the colors as true as it is reasonably possible to obtain in colored reproductions of this type. Colors in the photographs may differ from the color values cited in the detailed botanical description which accurately describe the colors of the new *Osteospermum.*

The photograph at the top of the sheet is a close-up view of a typical inflorescence of 'Sekiin47'.

The photograph at the bottom of the sheet comprises a side perspective view of a typical flowering plant of 'Sekiin47' grown in a container.

DETAILED BOTANICAL DESCRIPTION

The aforementioned photographs and following observations and measurements describe plants grown in Bonsall, Calif., in a polyethylene-covered greenhouse during the winter and under conditions typical of commercial *Osteospermum* production. During the production of the plants day temperatures ranged from 13 to 32° C. and night temperatures ranged from 10 to 16° C. Plants had been growing for about ten weeks in 15.25-cm containers when the photographs and the description were taken. Color references are made to The Royal Horticultural Society Colour Chart, 1995 edition, except where general terms of ordinary dictionary significance are used.

Botanical classification: *Osteospermum ecklonis* cultivar Sekiin47.

Parentage: Naturally-occurring whole plant mutation of the *Osteospermum ecklonis* cultivar Seikilrem, disclosed in U.S. Plant Pat. No. 13,407.

Propagation:

*Type.*—Terminal vegetative cuttings.

*Time to initiate rooting.*—About two weeks at 20° C.

*Time to develop roots.*—About four weeks at 20° C.

*Root description.*—Fine, fibrous and well-branched.

Plant description:

*Appearance.*—Perennial herbaceous container and garden plant. Compact and mounded plant habit; initially upright and then outwardly spreading. Freely branching habit, about four primary lateral branches and about twelve secondary lateral branches. Moderately vigorous growth habit.

*Plant height.*—About 21 cm.

*Plant width or area of spread.*—About 32 cm.

*Lateral branches.*—Length: About 20 cm. Diameter: About 5 mm. Internode length: About 2.2 cm. Aspect: Upright to outward. Strength: Strong. Texture: Smooth, glabrous. Color: 144A.

*Foliage description.*—Arrangement: Alternate; simple. Length: About 4.7 cm. Width: About 2.4 cm. Shape: Oblanceolate to spatulate. Apex: Rounded to broadly acute. Base: Attenuate. Margin: Entire with occasional tiny serrations. Venation pattern: Pinnate. Texture, upper and lower surfaces: Smooth, glabrous; glandular. Color: Developing and fully expanded foliage, upper surface: 147A. Developing and fully expanded foliage, lower surface: 147A. Venation, upper and lower surfaces: 148B. Petiole: Length: About 1.6 cm. Diameter: About 4 mm. Texture, upper and lower surfaces: Glabrous. Color, upper and lower surfaces: 147C.

Inflorescence description:

*Appearance.*—Terminal and axillary inflorescences held above and beyond the foliage on moderately strong peduncles. Composite inflorescence form, radially symmetrical, with ligulate-shaped ray florets and disc florets massed at the center; ray and disc florets arranged acropetally on a capitulum. Inflorescences persistent. Inflorescences face upright or outward.

*Flowering response.*—Plants flower continuous and freely from the spring through the fall.

*Postproduction longevity.*—Inflorescences maintain good color and substance for about seven to ten days on the plant.

*Quantity of inflorescences.*—Freely flowering; at one time, about five to six open inflorescences and inflorescence buds per lateral stem.

*Fragrance.*—None detected.

*Inflorescence bud.*—Length: About 1.8 cm. Diameter: About 1.1 cm. Shape: Ovoid. Color: 145A.

*Inflorescence size.*—Diameter: About 5.5 cm. Depth (height): About 1.5 cm. Disc diameter: About 1 cm. Receptacle height: About 2.4 cm. Receptacle diameter: About 2 cm.

*Ray florets.*—Length: About 3 cm. Width: About 6 mm. Shape: Ligulate. Apex: Slightly emarginate. Base: Attenuate. Margin: Entire. Texture, upper and lower surfaces: Smooth, glabrous; satiny. Orientation: Initially upright then close to horizontal; recurving slightly with development. Number of ray florets per inflorescence: About 20 in a single whorl. Color: When opening, upper surface: 14B. When opening, lower surface: 7A. Fully opened, upper surface: 14B; towards base, 93A to 93B; main color does not fade with development. Fully opened, lower surface: 13A.

*Disc florets.*—Shape: Tubular, elongated. Apex: Five-pointed. Length: About 8 mm. Width: At apex: About 1.5 mm. At base: About 1 mm. Number of disc florets per inflorescence: About 84. Color: Immature: 145D; towards the apex, 79A. Mature: Apex: 79A to 79B. Mid-section: 151A. Base: 145D.

*Phyllaries.*—Length: About 1.2 cm. Diameter: About 1 mm. Shape: Linear. Apex: Acuminate. Base: Fused. Margin: Entire. Texture, upper and lower surfaces: Slightly coarse. Number per inflorescence: About 22 in a single whorl. Color, upper and lower surfaces: 148A.

*Peduncles.*—Length, terminal peduncle: About 7.2 cm. Length, second peduncle: About 1.2 cm. Length, third peduncle: About 7 mm. Diameter: About 2 mm. Angle: Terminal peduncles, erect; secondary and tertiary peduncles, about 45° from vertical. Strength: Strong. Texture: Sparsely pubescent. Color: 144A.

*Reproductive organs.*—Androecium: Present on disc florets only. Stamen number: Five per floret; fused around style. Anther shape: Oblong. Anther length: About 1.5 mm. Anther color: 79A. Pollen amount: Scarce. Pollen color: 28A. Gynoecium: Present on both ray and disc florets. Pistil number: One per floret. Pistil length: About 6 mm. Stigma shape: Two-parted. Stigma color: 79A. Style length: About 3.5 mm. Style color: 79C. Ovary color: 145B.

*Seed/fruit.*—Seed and/or fruit production has not been observed.

Disease/pest resistance: Resistance to pathogens and pests common to *Osteospermums* has not been observed on plants grown under commercial greenhouse or outdoor conditions.

Temperature tolerance: Plants of the new *Osteospermum* have been observed to tolerate temperatures from 4 to 35° C.

It is claimed:

1. A new and distinct cultivar of *Osteospermum* plant named 'Sekiin47', as illustratred and described.

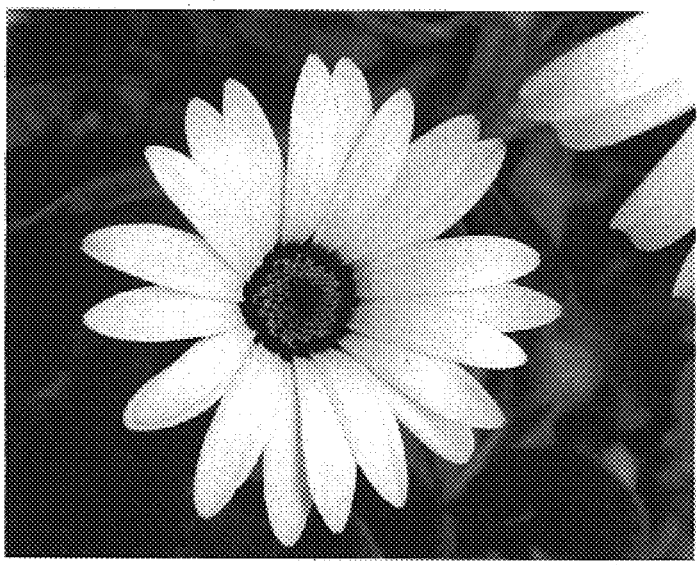
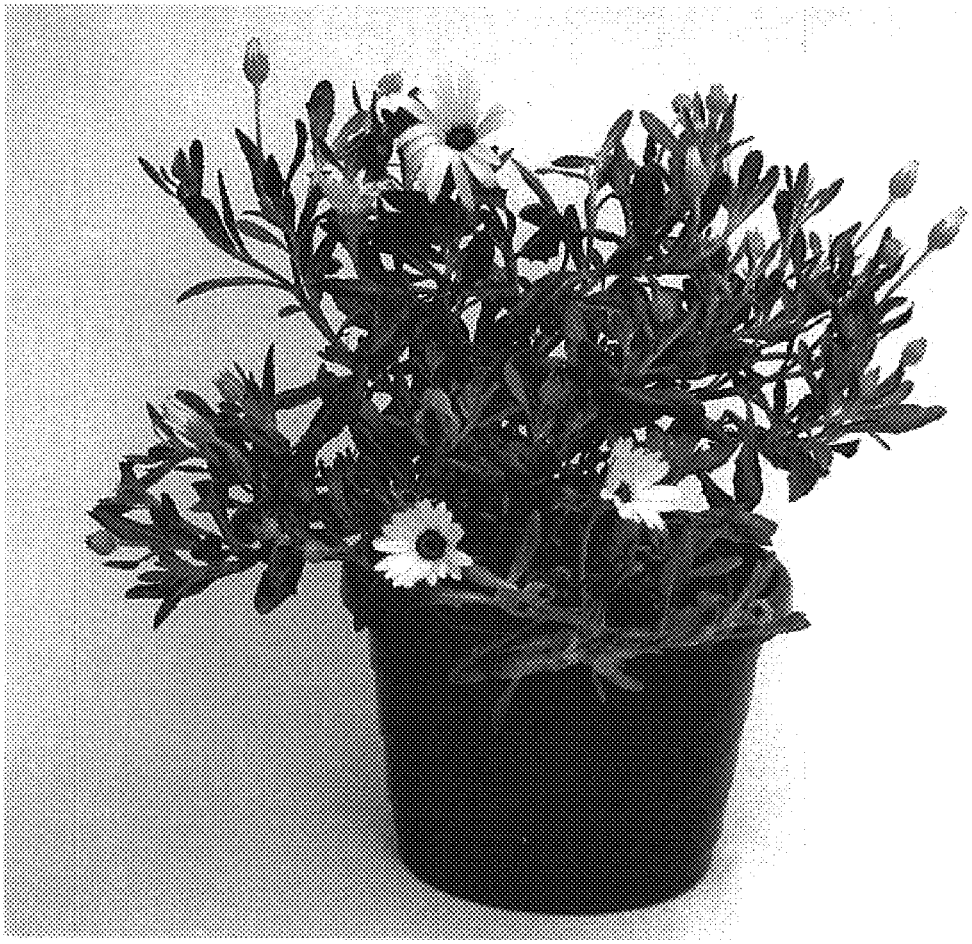

* * * * *